United States Patent
Herslöf et al.

(10) Patent No.: US 6,355,693 B1
(45) Date of Patent: *Mar. 12, 2002

(54) FRACTIONATED VEGETABLE OIL

(75) Inventors: Bengt Herslöf, Stockholm; Per Tingvall, Norberg; Carl-Gunnar Kroon, Stockholm, all of (SE)

(73) Assignee: Scotia Lipidteknik AB, Stockholm (SE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/029,932
(22) PCT Filed: Sep. 13, 1996
(86) PCT No.: PCT/SE96/01146
§ 371 Date: Mar. 9, 1998
§ 102(e) Date: Mar. 9, 1998
(87) PCT Pub. No.: WO97/11141
PCT Pub. Date: Mar. 27, 1997

(30) Foreign Application Priority Data

Sep. 22, 1995 (SE) .............................................. 9503296

(51) Int. Cl.[7] .......................... B01F 17/34; C11B 1/10; A23L 1/035; A61K 31/70
(52) U.S. Cl. .......................... 516/29; 516/73; 516/918; 424/776; 426/430; 554/14; 536/123.13; 536/128
(58) Field of Search ................................. 426/604, 425, 426/429, 492, 430, 655; 516/29, 73, 918, 204; 536/123.13, 4.1, 18.5, 128; 424/195.1, 776; 554/14, 12

(56) References Cited

U.S. PATENT DOCUMENTS

| | | | | | |
|---|---|---|---|---|---|
| 2,554,873 A | * | 5/1951 | Musher | ....................... | 426/655 |
| 2,636,888 A | * | 4/1953 | Washburn | .................... | 426/655 |
| 3,734,901 A | | 5/1973 | Hayes et al. | ................... | 554/13 |
| 4,517,120 A | * | 5/1985 | Roychoudhury | ............ | 426/655 |
| 5,026,548 A | * | 6/1991 | Evans et al. | ............. | 424/195.1 |

FOREIGN PATENT DOCUMENTS

| | | |
|---|---|---|
| EP | 0 290 156 | 11/1988 |
| WO | WO 95/20943 | 8/1995 |
| WO | WO 95/20944 | * 8/1995 |

OTHER PUBLICATIONS

V.L. Youngs, M. Puskulcu, and R.R. Smith, Oat Lipids. I. Composition and Distribution of Lipid Components in Two Oats Cultivars, *Cereal Chem.* 54(4): 803–812, (1977) Month Unknown.

* cited by examiner

*Primary Examiner*—Daniel S. Metzmaier
(74) *Attorney, Agent, or Firm*—Hoffmann & Baron, LLP

(57) ABSTRACT

A new method for producing a fractionated vegetable oil from a plant material. The plant material is extracted with a non-polar solvent and the solvent is evaporated giving a crude oil which includes non-polar and polar lipids. The crude oil is mixed with an alcohol at a controlled temperature and a resulting alcoholic phase is separated and evaporated to recover a polar lipid rich fractionated vegetable oil. The invention also refers to the use of the polar lipid rich fractionated vegetable oil as a surface active agent.

8 Claims, 1 Drawing Sheet

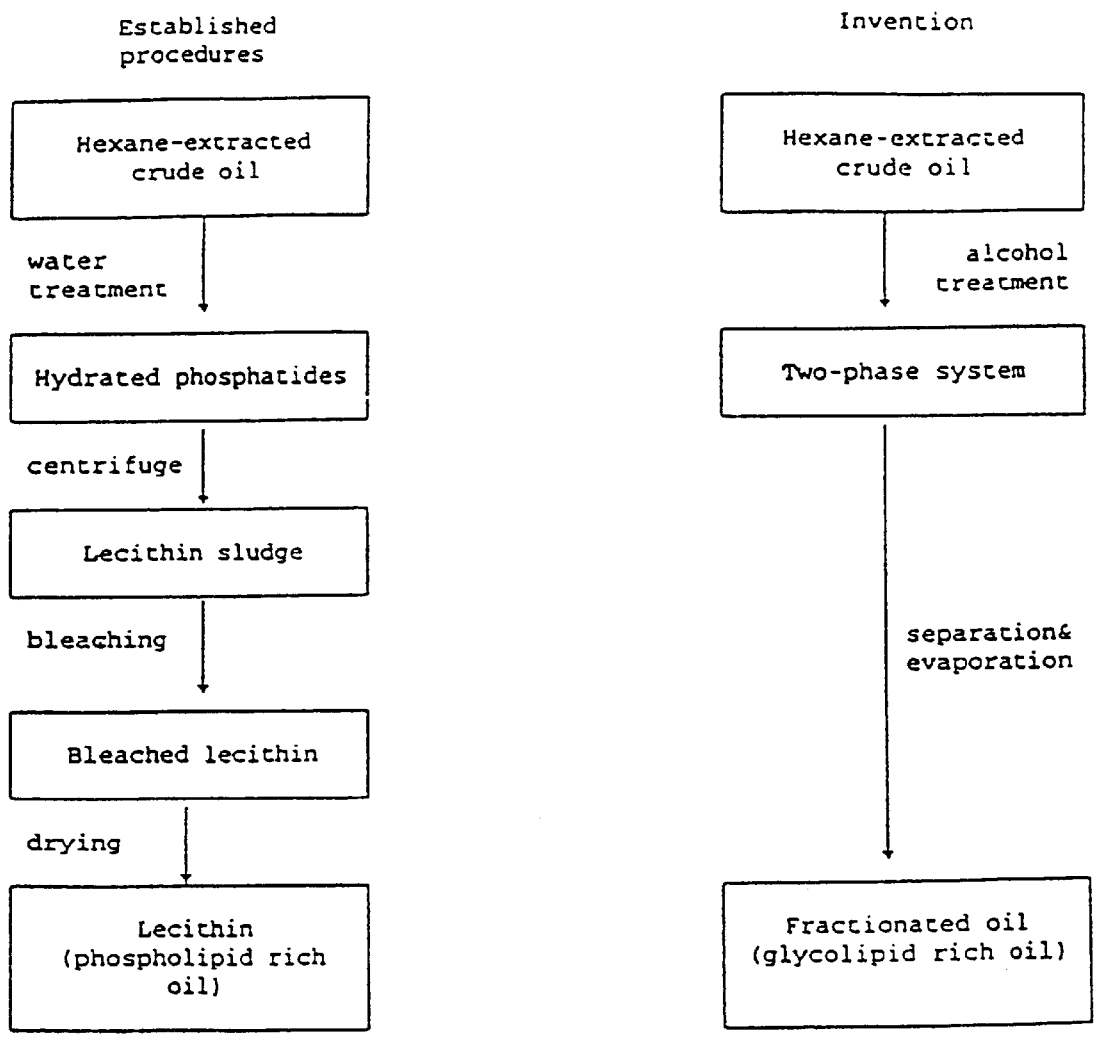
FIGURE

FRACTIONATED VEGETABLE OIL

This application is filed under 35 U.S.C. §371 and is based on PCT International Application No. PCT/SE96/01146 which was filed on Sep. 13, 1996.

TECHNICAL FIELD

This invention relates to an industrially applicable process for preparing a fractionated oil from crude vegetable oils, preferably from cereals and grains, the fractionated oil which is obtainable by said process, and to the use of the fractionated oil as a surface active agent in food, cosmetics and pharmaceutical products.

1. Background of the Invention

The production of vegetable oils from various sources, such as soybeans, rapeseed and corn, is based on extraction with as hexane and subsequent refining of the crude extracts to edible oils. The first step in the refining sequence is the so-called degumming, which step serves to separate the phosphatides by the addition of water. The material precipitated by degumming is separated and further processed to mixtures used under the name of lecithins. The commercial lecithins, such as soybean lecithin and sunflower lecithin, are semi-solid or very viscous materials, which consist of a mixture of polar lipids, mainly phospholipids, and oil, mainly triglycerides. These lecithins are by-products from the production of the corresponding vegetable oils and have, after further treatment and purification, found use as surface active materials in many applications, including food, cosmetics and pharmaceutical products.

Wide ranges of conditions for the degumming process are reported in the literature, all of them based on the addition of water, or water solutions, to the crude oils to hydrate the phosphatides and make them insoluble in the oil. Further processing of this crude precipitate, the so called lecithin sludge, involves centrifugation, that is desliming, bleaching by treatment with hydroperoxide and benzoyl peroxide, heat treatment, such as drying or cooking, to give the crude lecithin, which is used as ingredient mainly in food products. The crude lecithin can be further processed in various ways, the most common being purification, such as filtration and adsorption, deoiling, for instance by acetone fractionation to remove the neutral lipids, and fractionation, for instance by means of alcohol treatment to separate alcohol-soluble and alcohol-insoluble components. The established procedure for producing lecithin is shown in Figure.

The methods outlined above are mainly used to produce lecithins from oil crops, such as soybeans, sunflower, rapeseed, corn and cottonseed. In principle all of these are polar lipid rich oils, characterized by being phospholipid rich, particularly phosphatidylcholine rich, consisting of 40–60% oils and 60–40% polar lipids. The content of glycolipids in said lecithins is relatively small, but varies with the source, and the process is designed to give as high a yield as possible of phospholipids at the expense of the glycolipids and other components. Other sources than oil crops, for example cereals, contain more glycolipids than phospholipids.

Glycolipids are well known constituents of plant cell membranes. The most important classes of these contain one to four sugars linked glycosidically to diacylglycerol. The two most abundant classes contain one and two galactose units, respectively, and the commonly used nomenclature and abbreviations of these are mono- and digalactosyldiglyceride, MGDG and DGDG, sometimes referred to as galactolipids. The general structure of digalactosyldiglyceride, DGDG, is outlined below.

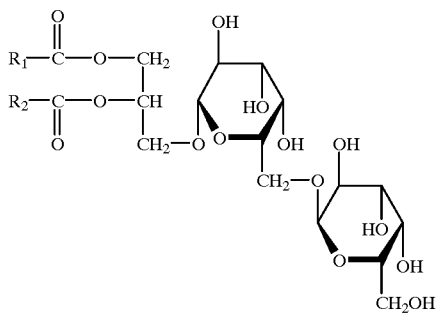

The commercial lecithins, such as lecithins produced from soybean oil, sunflower oil, and rapeseed oil, consist mainly of phospholipids, of which phosphatidylcholine (PC) and phosphatidylethanolamine (PE) are most abundant. PC is the most well characterized class of polar lipids and PC rich materials have found a wide range of industrial applications. Glycolipids have been identified as minor constituents of these lecithins. From an industrial viewpoint it is of a general interest and importance to have access to materials rich in polar lipids other than PC, and also, materials rich in polar lipids other than phospholipids, particularly glycolipids. This relates to the fact that PC and other phospholipid classes are charged, that is contain anionic or zwitterionic functional groups, while the glycolipids are non-charged.

2. Prior Art

There are numerous descriptions in the literature on the use, of lecithins, purified lecithins and phospholipids as surface active ingredients, see for instance "Lecithins: Sources, Manufacture & Uses", B. F. Szuhaj, Editor, American Oil Chemists' society, 1989.

CA 1102795 describes a method of isolating polar lipids from cereal lipids by the addition of at least 50% by weight of water. This method is a modified degumming in the sense that it utilises the principle of adding water to a crude oil mixture.

In Cereal Chem., 1977, vol. 54(4), pp 803–812, lipids were extracted from oat groats by means of diethyl ether and said ether extract evaporated to dryness and reextracted with water saturated n-butanol. After another evaporation the mixture was taken up in chloroform and the lipids obtained were analysed and recorded as bound lipids.

EP 0 290 156 refers to a process for extracting oilseeds by means of a combination of a polar and a non-polar extraction solvent in a counter-current system aiming at a high oil recovery.

Galactolipids, primarily DGDG and DGDG-rich materials have been investigated and found to be surface active material of interest in industrial applications such as food, cosmetics, and pharmaceutical products.

WO 95/20943 describes the use of DGDG-rich material, a "galactolipid material", as an emulsifier in oil-in-water emulsions for pharmaceutical, nutritional and cosmetic use. WO 95/20944 describes the use of said "galactolipid material" as a bilayer-forming material in polar solvents for pharmaceutical, nutritional and cosmetic use; and WO 95/20945 describes the use of the "galactolipid material" as a lipophilic carrier for pharmaceutical, nutritional and cosmetic use. The DGDG-rich material, the "galactolipid material", utilized in said applications was prepared from cereals by extraction of the lipids with ethanol and a subsequent purification on a chromatographic column to pure DGDG or a DGDG-rich fraction of polar lipids. The use of chromatography on a large-scale is expensive compared to the production of, for-example, soybean lecithin by degumming, and there is need for a cheaper way to produce polar lipid rich materials for industrial use, particularly glycolipid rich materials.

DESCRIPTION OF THE INVENTION

The present invention is related to a novel method for producing a fractionated vegetable oil from a plant material.

The present invention provides a novel method for producing purified lecithins or a polar lipid rich fractionated oil, particularly rich in glycolipids, which without further purification can be directly utilized as a surface active agent, for example as an emulsifier in food, cosmetics and pharmaceutical products. The method of the present invention is designed to maintain the concentration of the glycolipids, which implies that the polar lipid rich fractionated vegetable oils obtainable in accordance with the invention are glycolipid rich, particularly digalactosyldiglyceride rich oils. The concentration of the polar lipids can be controlled by process parameters.

In the novel, industrially applicable method of the invention, for producing a polar lipid rich fractionated vegetable oil, a plant material is extracted with a non-polar solvent, and the solvent is evaporated giving a crude oil comprising non-polar and polar lipids, which crude oil is further purified. The method of the invention is characterized in that the crude oil is mixed with an alcohol at a controlled temperature, the alcoholic phase is separated and evaporated and a polar lipid rich fractionated vegetable oil is obtained.

The method of the invention can be described by the following steps:

(a) extraction of a plant material with a non-polar solvent and evaporation of the solvent to obtain a crude oil comprising non-polar and polar lipids, (b) obtaining a two-phase system by mixing the crude extract with an alcohol, and (c) obtaining a polar lipid rich fraction by collecting the alcoholic phase and evaporating the alcohol.

The invention is of particular industrial importance for the production of glycolipid rich fractionated oils from cereals and grains, especially oats.

Non-polar solvents are generally water-immiscible solvents, such as saturated or non-saturated, branched or linear alkanes. A preferred non-polar solvent is hexane of industrial grade.

Preferred alcohols to be used in the method of the invention for mixing with the crude oil are aliphatic alcohols having 1–8 carbon atoms, preferably 1–4 carbon atoms, for example methanol, ethanol, propanol and isopropanol.

The alcohol can be used as such or in admixture with water or other polar solvents. In a preferred method the alcohol is used in admixture with up to 35% by weight water, preferably 2.5–20% water.

In the method of the invention the crude oil is preferably mixed with at least equal volumes of alcohol at elevated temperatures.

In a preferred method of the invention the crude vegetable oil is obtained by extraction of oat kernels with industrial hexane. After removal of the solvent the crude extract is mixed with 2 volumes of ethanol (93% by weight in water) at 50° C. The upper ethanol-phase is separated from the lower oil-phase at 35° C. and the ethanol is evaporated. The remaining oily liquid is the fractionated oil, comprising 40% by weight of polar lipids (of which 79% is glycolipids) and 60% by weight of non-polar lipids, which is used as an emulsifier (1–5% by weight) in a oil-in-water emulsion of evening primrose oil (5–40% by weight) in water.

The method of alcohol treatment included in the invention must be clearly distinguished from the well-known industrial treatment of various lecithins with alcohol (cf. "Lecithins: Sources, Manufacture & Uses", B. F. Szuhaj, Editor, American Oil Chemists, Society, 1989; Chapter Seven: Fractionation and Purification of Lecithin). The purpose of such a process is to fractionate the lecithins in alcohol-soluble and non-alcohol-soluble components, consisting mainly of PC (alcohol-soluble) and PE (non-alcohol-soluble), respectively. The method of the present invention does not require any degumming step, which is a major advantage, and can furthermore surprisingly be performed, by appropriate adjustment of the proportions of alcohol to the crude oil and the temperature, to give a predicted concentration of the amount of polar lipids, and thus glycolipids, in the fractionated oil.

A fractionated vegetable oil which has been obtained by the method of the invention is characterized in containing 10–90% by weight of polar lipids, preferably 20–75%, and a remainder of non-polar lipids.

A fractionated vegetable oil which has been obtained by a method of the invention is preferably also characterized in containing more than 5% by weight, preferably more than 20%, glycolipids. Said fractionated vegetable oil also preferably contains more than 3% by weight, preferably more than 15%, DGDG.

The invention further relates to the use of this fractionated vegetable oil without further purification, as a surface active agent for preparing oil-in-water emulsions, water-in-oil emulsions and similar dispersions, reverse vesicles, microemulsions and other organised solutions.

The fractionated vegetable oil obtained by a method according to the invention can also be used as a surface active agent for the formulation of a food, pharmaceutical, skin care or other product for oral, enteral, parenteral, topical or any other form of administration.

The fatty material of these emulsions, other systems and organised solutions can be vegetable oils of all types, such as oils from the seeds and beans of soybean, sunflower, rapeseed (canola), palm, corn, safflower, evening primrose, borage, groundnut, sesame, and similar, furthermore animal oils and fats such as fish oils, liver oils, egg oils, and similar, further-more glycerides, fatty acids, esters and other substances, obvious to a person skilled in the art, which can be emulsified using the fractionated oil.

Preferred oils to be emulsified are selected from a triacylglycerol oil, preferably evening primrose oil or fractions thereof, borage oil or fractions thereof, or other vegetable oils or fractions thereof.

The fractionated oil of the invention, prepared according to the preferred process, consists of a wide range of polar and amphiphilic lipids in a continuous triglyceride phase. It has a low viscosity and a clear appearance. This makes the fractionated oil extremely easy to use as an emulsifier: the fractionated oil is simply added to the oil to be emulsified and the mixture is then gently mixed—no time is needed for swelling of the emulsifier in the oil phase as is the case for conventional, solid or amorphous lecithins.

The highly lipophilic properties of the fractionated oil of the invention are also beneficial from a practical point of view: no atmospheric water and oxygen are taken up during storage which may cause chemical degradation. Furthermore, due to its low viscosity the fractionated oil is easily pumped and thus easily dosed when used in large-scale production of emulsions.

Oil-in-water emulsions are prepared by using the fractionated oil either as the sole emulsifier or in combination with other amphiphilic compounds, as co-surfactants. The oil-in-water emulsion may also comprise optional additives known in the art for improving different aspects of the composition, such as flavouring agents, sweeteners, colorants, thickening agents, preservatives, antioxidants, etc.

Oil-in-water emulsions are prepared by conventional methods. For example, a 30 wt % emulsion of a triacylglycerol oil in water is prepared by adding the emulsifier, that is the fractionated oil, to the oil. The oil phase may also contain oil-soluble additives such as antioxidants and flavours. The total emulsifier concentration is 4 wt %. The oil phase is then gently mixed. The continuous phase may be pure water or an aqueous solution containing water-soluble additives such as sugar, flavours, and preservatives. If necessary, the pH of the aqueous phase is then adjusted. The oil phase as well as the aqueous phase are preheated and then the oil phase is added to the aqueous phase under high-shear mixing. The pre-emulsion is then subjected to high-pressure homogenisation.

The ratio between fractionated oil and oily material in an oil-in-water emulsion could preferably be within-the range of 1:20–1:1 by weight, especially 1:10–1:3 by weight. The total content of oily material in the oil-in-water emulsion is less than 50 wt%, preferably less than 30 wt %.

In addition, the emulsification capacity of the fractionated oil of the invention is surprisingly high; the amount needed for making a 40 wt % oil-in-water emulsion based on evening primrose oil may be as low as 3 wt %, corresponding to approximately 1.3 wt % polar lipids. As a comparison, WO 95/20943 discloses a way of using a polar lipid fraction in an amount of 2 wt % for emulsifying the same type of emulsion.

Conventional fat emulsions based on soybean or egg phospholipids and triglyceride oils may require 1.2 wt % emulsifier for 20 wt % oil-in-water emulsion.

At higher contents of oily material it is possible to obtain oil continuous systems, i.e. systems in which droplets of pure water or aqueous solution are dispersed in the oil phase by means of the fractionated oil. Depending on, inter alia, the content of fractionated oil, the weight ratio between oil and water and the water content, the following organised solutions may be obtained (with decreasing water content): water-in-oil emulsion, reverse micelles (known as an $L_2$ phase or a microemulsion), and reverse vesicles.

The invention also comprises any food, nutritional, pharmaceutical, dermatological, cosmetic or other composition, involving emulsions, microemulsions, reverse vesicles or other forms of preparations, which utilises in its preparation the fractionated vegetable oil prepared according to the invention.

Another advantage of the present invention is its pleasant taste which makes it suitable for use in enteral emulsions.

These oil-rich systems are particularly useful in topical skin care preparations, both medicinal topical skin care preparations and cosmetological preparations. As exemplary topical skin care preparations may be mentioned various ointments containing one or,more active ingredients.

The fractionated oil can also be used as such in practical applications, or mixed with an oil, without adding water or an aqueous solution. As an example, a mixture of 3 wt % salicylic acid in a blend of fractionated oil and a triglyceride oil, such as peanut oil, may be used as a medicinal preparation for treating psoriasis of the scalp.

A preferred pharmaceutical or nutritional composition comprises γ-linolenic acid, GLA, or other fatty acids, in the form of a free acid, its salts or esters as emulsified oil. Said pharmaceutical composition can in addition comprise another therapeutically active substance.

DESCRIPTION OF THE DRAWINGS

Figure shows a comparison between an established procedure for preparing lecithins and the process of the invention for preparing a fractionated oil.

EXAMPLES

Chemical Characterisation of the Fractionated Oil

Lipid class analysis was performed by high performance liquid chromatography, HPLC, using a column packed with diol-modified silica (Lichrosphere 100 DIOL, 5 μm, 250 mm×4 mm i.d.; E. Merck, Germany) The column was enclosed in a water bath held at 75° C. The analytical system consisted of a HPLC pump CM 4000 LDC/Milton Roy, USA), and an injector, model 7125, with a 20 μl injection loop (Rheodyne Inc., USA). The evaporative light-scattering detector used was a Sedex 45 (S.E.D.E.R.E., France) equipped with a Sedex 55 nebulisation chamber with a drift tube temperature and air inlet pressure of 97° C. and 2.0 bar, respectively.

The flow of the mobile phase was 1 ml/min during the analysis. A binary solvent gradient, linear over 25 min, was used starting with 100% of A and ending with 100% of B, where A=hexane:isopropanol:n-butanol:tetrahydrofuran:isooctane: water, 64:20:6:4.5:1, and B=isopropanol: n-butanol: tetrahydrofuran: isooctane: water, 75:6:4.5:4.5:10. All solvents contained ammonium acetate, 180 mg/l.

Data collection and processing were done with GynkoSoft Data system version 4.22 (Softron GmbH, Germany). A typical amount injected for analysis was 100 μg. Identification was based on retention time comparison with authentic standards, such as MGDG and DGDG (Sigma Chemical Co., USA). Volatile compounds were not detected in this system. Quantification was based on peak area calculations.

Example 1

Extraction of Crude Oil from Oat Flakes 400 g of oat flakes (AXA Kungsörnen, Järna) were mixed with 2 l of industrial hexane (KEBO, Stockholm). The mixture was gently stirred for 1 h at a temperature of 45° C. The extract was filtered through a Munktell paper filter, quality 1003. The extract was evaporated in a rotatory evaporator. The yield of crude oat oil was 22.4 g (5.6 wt %).

Example 2

Fractionation of Oat Oil with Isopropanol 2 ml (1.84 g) of the crude oat oil obtained in Example 1 were mixed with 8 ml of industrial isopropanol (85% KEBO, Stockholm) in a test tube. The tube was shaken for 30 seconds and the mixture was then allowed to separate for one hour. The upper phase, 8 ml, was transferred to an evaporating flask and evaporated in a rotatory evaporator. The yield of fractionated oat oil was 0.28 grams (15 wt %). The concentration of polar lipids was 44 wt %, as determined by HPLC. Of the polar lipids 77.4% (area) consisted of glycolipids and 76.4% (area) was DGDG.

Example 3

Fractionation of Oat Oil with Ethanol 13 l of crude oat oil (12 kg, temperature 20° C.) were mixed under stirring with 26 l of ethanol (95% by volume in water), which was preheated to 50° C. The mixture was stirred for 30 min at 48–52° C. The mixture was then allowed to separate at a temperature of 40° C. The lower phase (14 l) was removed. The upper phase was heated under stirring to 55° C. to obtain a clear solution. The solution was filtered through a sterile filter and the ethanol was evaporated in a falling film evaporator. The yield of fractionated oat oil was 1845 g (15 wt %), which contained 40 wt % polar lipids, of which 81% (area) was glycolipids and 76.3% (area) was DGDG.

TABLE 1

Composition of a fractionated oil from oat

| | % (weight) |
|---|---|
| Overall composition: | |
| polar lipids | 40 |
| oil | 60 |

| | % (area) |
|---|---|
| Polar lipid composition: | |
| glycolipids | 80.7 |
| phospholipids | 14.5 |
| other polar lipids | 4.8 |
| Glycolipid composition: | |
| DGDG | 76.3 |
| other glycolipids | 4.4 |

Control of the Chemical Composition

By changing the values of the process parameters of the preparation method of the invention it is possible to obtain a fractionated oil with desired composition. For example, if the goal is to produce a fractionated oil containing a polar lipid level of 17% the control parameters should be set at isopropanol (68% in water, v:v), 50% oil loading at 41° C. and a blending time of 30 seconds. If, however, a fractionated oil containing 32% polar lipid level is desired the control parameters should be set at ethanol (93% in water v:v), 20% oil loading at 50° C. and a blending time of 90 seconds. In the same way a polar lipid level of 64% can be obtained by setting the control parameters at isopropanol (75% in water, v:v), oil loading of 33% at 23° C. with a blending time of 15 seconds. Furthermore, as can be seen in Table 2, the relative levels of glycolipids and especially DGDG are constant, regardless of the process conditions. The polar lipid concentration can thereby be predicted at a reasonable level of certainty, with a constant level of glycolipids.

TABLE 2

| Run | Ethanol (%) in water | Isopropanol (%) in water | Oil loading (%) | Temperature (° C.) | Blending time (x15s) | Total polar-lipid (%) | Polar lipid composition (%) | |
|---|---|---|---|---|---|---|---|---|
| | | | | | | | Glycolipids | DGDG |
| 1 | | 68 | 50 | 41 | 2 | 17 | 78 | 75 |
| 2 | 96 | | 20 | 50 | 2 | 22 | 81 | 77 |
| 3 | | 93 | 30 | 30 | 4 | 27 | 82 | 79 |
| 4 | 96 | | 40 | 50 | 6 | 28 | 83 | 80 |
| 5 | 93 | | 20 | 50 | 6 | 32 | 81 | 78 |
| 6 | 92 | | 30 | 37.5 | 4 | 37 | 85 | 81 |
| 7 | | 85 | 20 | 20 | 2 | 44 | 78 | 74 |
| 8 | | 83 | 30 | 30 | 4 | 49 | 79 | 76 |
| 9 | | 75 | 33 | 60 | 3 | 58 | 78 | 75 |
| 10 | | 75 | 33 | 23 | 1 | 64 | 80 | 76 |
| Average | | | | | | | 81 | 77 |
| Std. Dev. | | | | | | | | |

Example 4

Preparation of a 39% Oil-in-water Emulsion

The fractionated oat oil from Example 3 was used to produce an oil-in-water emulsion in the way described below.

| Ingredients: | | | |
|---|---|---|---|
| Oil phase | (g) | Water phase | (g) |
| Evening primrose oil | 118.39 | Sugar | 45.00 |
| Fractionated oat oil | 15.00 | Potassium sorbate | 0.60 |
| Ammonium phosphatides | 0.30 | Benzoic acid | 0.30 |
| Ascorbyl palmitate | 0.06 | Nescafé | 3.00 |
| Tocopheryl acetate | 3.27 | Coffee flavour | 1.50 |
| | | Water | 112.58 |
| Total | | | 300.00 |

The oil phase and the water phase were prepared separately. Both phases were preheated to 60° C. and the oil phase was added to the water phase under high-shear mixing at 15,000 rpm for 7 min. The pH was adjusted to 4.5 during the mixing using 50 wt % citric acid solution. The mixture was homogenized at 500 bar and approximately 60° C. for 8 cycles (Rannie homogenizer, Model LAB, Type 12.51H; APV Rannie AS, Denmark).

Example 5

Preparation of Three Oil-in-water Emulsions

| Ingredients: | A (g) | B (g) | C (g) |
|---|---|---|---|
| Oil phase | | | |
| Evening primrose oil | 118.38 | 118.38 | 1183.8 |
| Fractionated oil | 5.91 | 11.85 | 147.9 |
| Ammonium phosphatides | 0.30 | 0.30 | 3.0 |
| Ascorbyl palmitate | 0.06 | 0.06 | 0.6 |
| Tocopheryl acetate | 3.27 | 3.27 | 32.7 |
| Water phase | | | |
| Sugar | 45.00 | 45.00 | 450.0 |
| Potassium sorbate | 0.60 | 0.60 | 6.0 |
| Benzoic acid | 0.30 | 0.30 | 3.0 |
| Water | 126.18 | 120.24 | 1173.0 |
| Total | 300.00 | 300.00 | 3000.00 |

The emulsions were prepared according to Example 4 and samples were taken after different numbers of cycles in the high-pressure homogeniser. The different emulsions were analyzed with respect to physical stability and by particle size and size distribution measurements after storage at different temperatures. Particle size and size distribution measurements were measured by means of a dynamic light scattering instrument (Zetasizer 4, Malvern Instruments, UK) and are reported as z averages and polydispersity indices, respectively, where the latter is interpreted as the variance of a supposed log-normal model. A low polydispersity index value indicates a narrow size distribution of the emulsion droplets, which is preferred in many applications. The "creaming" phenomenon is a step in the emulsion breakdown process where flocculated droplets coalesce. Eventually, creaming may lead to a phase separation observed as an oily layer on top of the emulsion and a water layer on the bottom. The results are summarised in Table 3.

TABLE 3

| Emulsion | No. of cycles | Temp. | Fractionated oil (wt %) | Visual observ. | Particle size (nm) | Polydisp. index | Measured after (days) |
|---|---|---|---|---|---|---|---|
| A | 5 | +4° C. | 1.97 | OK | 453 | 0.205 | 6 |
| A | 5 | RT | 1.97 | creaming | 459 | 0.153 | 6 |
| A | 5 | +40° C. | 1.97 | creaming | 472 | 0.231 | 6 |
| A | 5 | RT | 1.97 | creaming | 481 | 0.229 | 12 |
| A | 5 | +40° C. | 1.97 | creaming | 450 | 0.225 | 12 |
| B | 5 | | 3.95 | OK | 316 | 0.080 | 0 |
| B | 4 | | 3.95 | OK | 342 | 0.074 | 0 |
| B | 3 | | 3.95 | OK | 364 | 0.125 | 0 |
| B | 5 | RT | 3.95 | OK | 362 | 0.132 | 6 |
| B | 5 | 40° C. | 3.95 | OK | 341 | 0.123 | 6 |
| C | 8 | RT | 4.93 | OK | 270 | 0.061 | 12 |
| C | 6 | RT | 4.93 | OK | 290 | 0.066 | 12 |
| C | 4 | RT | 4.93 | OK | 299 | 0.056 | 12 |
| C | 2 | RT | 4.93 | OK | 368 | 0.097 | 12 |
| C | 8 | RT | 4.93 | OK | 268 | 0.054 | 20 |
| C | 8 | +40° C. | 4.93 | OK | 266 | 0.053 | 20 |

RT = room temperature; OK = stable emulsion

Example 6

Preparation of Oil-in-water Emulsions of GLA Enriched Evening Primrose Oil, DLMG

| Ingredients: | D (g) | E (g) |
|---|---|---|
| Oil phase | | |
| DLMG 25 (Callanish Ltd., UK) | 90.00 | 120.00 |
| Fractionated oil | 15.00 | 15.00 |
| Ammonium phosphatides | 0.30 | 0.30 |
| Ascorbyl palmitate | 0.06 | 0.06 |
| Tocopherol acetate | 3.27 | 3.27 |
| Water phase | | |
| sugar | 36.00 | 36.00 |
| potassium sorbate | 0.60 | 0.60 |
| benzoic acid | 0.30 | 0.30 |
| water | 154.47 | 124.47 |
| Total | 300.00 | 300.00 |

The emulsions were prepared and characterised immediately after preparation according to Example 5. The results are sum-merized in Table 4.

TABLE 4

| Emulsion | No. of cycles | Temp. | Fractionated oil (wt %) | Visual observ. | Particle size (nm) | Polydisp. index |
|---|---|---|---|---|---|---|
| D | 5 | RT | 5 | OK | 207 | 0.090 |
| E | 5 | RT | 5 | OK | 258 | 0.051 |

RT = room temperature;
OK = stable emulsion

Example 7

Preparation of a 30 wt % Oil-in-water Emulsion with Evening Primrose Oil (batch size 40 kg)

| Ingredients: | kg |
|---|---|
| Aqueous phase | |
| Water | 18.4 |
| Sucrose | 7.6 |
| Oil phase | |
| Evening primrose oil (Callanish Ltd., UK) | 12.0 |
| Fractionated oil | 2.0 |

Sucrose was dissolved in the water during high-shear mixing. The fractionated oil was mixed with the evening primrose oil with a ladle. The oil phase was then added to the aqueous phase under high-shear mixing for 6 min. The pre-emulsion formed was further mixed for 30 min using the high-shear mixer. The pre-emulsion was then transferred to the storage container of a high pressure homogeniser (Model SHL05; Tetra Laval AB, Sweden) and then homogenised at 400 bar for 120 min at a flow rate of 120 l/h (corresponding to approximately 6 cycles).

This resulted in a fine, stable emulsion with an average particle size of 249 nm. After storing the emulsion at room temperature for six months neither phase separation nor creaming occurred, implying a long shelf life of the product.

The emulsion can be sterilised in different ways, e.g. by means of heat sterilisation in a rotatory autoclave or by ultra high temperature (UHT) treatment. This type of emulsion is particularly suitable for food applications and as a carrier of oral delivery of drugs since no preservatives are present which may have a negative effect on the palatability.

Example 8

Preparation of 20 wt % Emulsions with Evening Primrose Oil and Different Emulsifiers (batch size 300 g)

| Ingredients: | F (wt %) | G (wt %) | H (wt %) |
|---|---|---|---|
| Purified water | 46.39 | 46.54 | 46.60 |
| Evening primrose oil | 30.21 | 30.04 | 30.02 |
| Sucrose | 18.93 | 18.99 | 19.00 |
| Emulsifier: | | | |
| Fractionated oil, batch A | 4.05 | | |
| Fractionated oil, batch B | | 4.01 | |
| Soya lecithin | | | 4.00 |
| Potassium sorbate | 0.20 | 0.20 | 0.20 |
| Ammonium phosphatides (E 442) | 0.10 | 0.10 | 0.10 |
| Orange flavour | 0.10 | 0.10 | 0.11 |
| Ascorbyl palmitate | 0.02 | 0.02 | 0.02 |

The soybean lecithin used was Topcithin 100 from Lucas Meyer, Germany, with a total content of 38.2 wt % polar lipids. Ascorbyl palmitate and the ammonium phosphatides were mixed with a small amount of the oil at 40° C. The mixture was then cooled to room temperature and dispersed in the rest of the oil. The oil-phase was then added to the aqueous phase under high-shear mixing at 15,000 rpm for 15 min. The pre-emulsion was adjusted to pH 4.9 using 50 wt % phosphoric acid. It was then homogenised at 500 bar for 6 cycles (Rannie homogenizer, Model Mini-Lab 8.30 H, APV Rannie AS, Denmark) with cooling to room temperature after each cycle.

The emulsions were then stored at 40° C. in 10 ml glass vials. The following observations were then made:

| | One week | One month |
|---|---|---|
| Emulsion F | 2 mm creaming | 3 mm creaming |
| Emulsion G | 2 mm creaming | 2 mm creaming |
| Emulsion H | 1 mm oily layer on top of the vial | 7 mm oily layer on top, 2 mm of water on the bottom |

These data imply that the fractionated oil of the invention is a more efficient emulsifier than a conventional soybean lecithin as it forms a more stable emulsion.

Example 9

Preparation of 40 wt % Emulsions with Fractionated Palm Oil (batch size 300 g)

| Ingredients | wt % |
|---|---|
| Water | 58.0 |
| CPL Palm oil (Scotia LipidTeknik AB, Sweden) | 40.0 |
| Fractionated oil | 2.0 |

The palm oil was melted at 50° C. and mixed with the fractionated oil. The oil phase and the water were preheated to 65–70° C. and then the oil phase was added to the water under high-shear mixing at 15,000 rpm for 4 min. The pre-emulsion was then divided into two parts; one part was homogenised at 400 bar, the other part at 800 bar, both for 6 cycles at 60° C. (Rannie homogenizer, Model Mini-Lab 8.30 H, APV Rannie AS, Denmark).

Both parts of the preparation resulted in emulsions with a similar cream-like consistency. The average particle size (Z average) was in both cases around 480 nm (Zetasizer 4, Malvern Instruments, UK).

What is claimed is:

1. A method for producing a polar lipid rich fractionated vegetable oil from plant material, which is useful as a surface active agent, said method consisting essentially of:
   a. extracting plant material with a non-polar solvent to obtain a crude oil comprising non-polar and polar lipids;
   b. mixing said crude oil with an alcohol at a controlled temperature to provide a two-phase system consisting of an alcohol phase and an oil phase;
   c. recovering said alcohol phase from said two-phase system;
   d. evaporating said alcohol from said alcohol phase to provide said polarhlipid rich fractionated vegetable oil; and
   e. in the absence of further purification or degumming prior to using said polar lipid rich fractionated vegetable oil as a surface active agent.

2. A method according to claim 1, wherein said plant material is cereal or grains.

3. A method according to claim 2, wherein said cereal or grains are oats.

4. A method according to claim 1, wherein said alcohol is selected from the group consisting of methanol, ethanol, propanol and isopropanol.

5. A method according to claim 1, wherein said alcohol is admixed with up to 35% by weight of water.

6. A method according to claim 5, wherein said water is present in an amount of from about 2.5% to about 20% by weight.

7. A method according to claim 1, wherein said crude oil is mixed with at least an equal volume of ethanol.

8. A method according to claim 1, which further comprises adding said fractionated vegetable oil as a surface active agent to one of food, cosmetics and pharmaceuticals.

* * * * *

UNITED STATES PATENT AND TRADEMARK OFFICE
CERTIFICATE OF CORRECTION

PATENT NO.     : 6,355,693 B1                                         Page 1 of 1
DATED          : March 12, 2002
INVENTOR(S)    : Herslof et al.

It is certified that error appears in the above-identified patent and that said Letters Patent is hereby corrected as shown below:

Column 8,
Table 2, should read as follows:

TABLE 2

| Run | Ethanol (%) in water | Iso-propanol (%) in water | Oil loading (%) | Temperature (°C.) | Blending time (x15s) | Total polar lipid (%) | Polar lipid composition (%) | |
|---|---|---|---|---|---|---|---|---|
| | | | | | | | Glyco-lipids | DGDG |
| 1 | | 68 | 50 | 41 | 2 | 17 | 78 | 75 |
| 2 | 96 | | 20 | 50 | 2 | 22 | 81 | 77 |
| 3 | | 93 | 30 | 30 | 4 | 27 | 82 | 79 |
| 4 | 96 | | 40 | 50 | 6 | 28 | 83 | 80 |
| 5 | 93 | | 20 | 50 | 6 | 32 | 81 | 78 |
| 6 | 92 | | 30 | 37.5 | 4 | 37 | 85 | 81 |
| 7 | | 85 | 20 | 20 | 2 | 44 | 78 | 74 |
| 8 | | 83 | 30 | 30 | 4 | 49 | 79 | 76 |
| 9 | | 75 | 33 | 60 | 3 | 58 | 78 | 75 |
| 10 | | 75 | 33 | 23 | 1 | 64 | 80 | 76 |
| Average | | | | | | | 81 | 77 |
| Std. Dev. | | | | | | | 2 | 2 |

Column 11,
Example 8 - table should read as follows:

Example 8

Preparation of 20 wt% Emulsions with Evening Primrose Oil and Different Emulsifiers (batch size 300 g)

| | F (wt%) | G (wt%) | H (wt%) |
|---|---|---|---|
| Ingredients: | | | |
| Purified water | 46.39 | 46.54 | 46.60 |
| Evening primrose oil | 30.21 | 30.04 | 30.02 |
| Sucrose | 18.93 | 18.99 | 19.00 |
| Emulsifier: | | | |
| Fractionated oil, batch A | 4.05 | | |
| Fractionated oil, batch B | | 4.01 | |
| Soya lecithin | | | 4.00 |
| Potassium sorbate | 0.20 | 0.20 | 0.20 |
| Ammonium phosphatides (E 442) | 0.10 | 0.10 | 0.10 |
| Orange flavour | 0.10 | 0.10 | 0.11 |
| Ascorbyl palmitate | 0.02 | 0.02 | 0.02 |

Signed and Sealed this

Twenty-first Day of January, 2003

JAMES E. ROGAN
*Director of the United States Patent and Trademark Office*